United States Patent
Brower et al.

(10) Patent No.: US 7,238,535 B2
(45) Date of Patent: Jul. 3, 2007

(54) TEST CELL FOR EVALUATING PHOSPHOR

(75) Inventors: Karen Ruth Brower, Chandler, AZ (US); Roy Scott Chancellor, Scottsdale, AZ (US); William A. Coghlan, Tempe, AZ (US); Will Melvell Hooke, Jr., Tempe, AZ (US); Curtis Henry Kempton, Higley, AZ (US); Alan C. Thomas, Gilbert, AZ (US)

(73) Assignee: World Properties, Inc., Lincolnwood, IL (US)

( * ) Notice: Subject to any disclaimer, the term of this patent is extended or adjusted under 35 U.S.C. 154(b) by 345 days.

(21) Appl. No.: 10/931,827

(22) Filed: Sep. 1, 2004

(65) Prior Publication Data

US 2006/0046307 A1     Mar. 2, 2006

(51) Int. Cl.
    *G01N 21/64*     (2006.01)
    *G01N 21/01*     (2006.01)

(52) U.S. Cl. ............ 436/172; 422/58; 422/82.05; 422/82.07; 422/104; 436/165

(58) Field of Classification Search ............ 422/58, 422/82.05, 82.07, 99, 104; 436/165, 172
See application file for complete search history.

(56) References Cited

U.S. PATENT DOCUMENTS

| | | | | |
|---|---|---|---|---|
| 2,015,949 A | * | 10/1935 | Maw | 356/246 |
| 2,056,791 A | * | 10/1936 | Logan | 356/246 |
| 2,302,830 A | * | 11/1942 | Axelrad | 359/398 |
| 2,673,789 A | * | 3/1954 | Brown | 422/99 |
| 3,521,964 A | * | 7/1970 | Wilks, Jr. | 356/246 |
| 3,565,537 A | * | 2/1971 | Fielding | 356/246 |
| 3,814,522 A | * | 6/1974 | Clark et al. | 356/246 |
| 3,879,106 A | * | 4/1975 | McCormick | 359/398 |
| 4,321,330 A | * | 3/1982 | Baker et al. | 435/305.1 |
| 4,427,634 A | * | 1/1984 | Truglio | 422/99 |
| 4,513,023 A | | 4/1985 | Wary | 427/54.1 |
| 4,564,503 A | * | 1/1986 | Greisch | 422/104 |
| 4,569,647 A | * | 2/1986 | McCormick | 425/117 |
| 4,595,561 A | * | 6/1986 | Thornton et al. | 422/58 |
| 4,654,197 A | * | 3/1987 | Lilja et al. | 204/403.02 |
| 4,682,890 A | * | 7/1987 | de Macario et al. | 356/244 |

(Continued)

OTHER PUBLICATIONS

Ylilammi, M. et al, IEEE Transactions on Electron Devices 1995, 42, 1227-1232.*

(Continued)

*Primary Examiner*—Arlen Soderquist
(74) *Attorney, Agent, or Firm*—Paul F. Wille

(57) ABSTRACT

An test cell is adapted for both making and testing samples. The cell includes a bottom plate and a top plate having concentric apertures defining a central test cavity. A post attached to the bottom plate closes off the bottom of the test cavity. A slide closes off the top of the test cavity. The top of the post is spaced slightly from the underside of the slide to define a test cavity of substantially uniform thickness. The test cavity is filled with phosphor suspended in uncured resin, closed, and the resin is cured. Once cured, the sample is stable, although delicate, and can be re-measured several times with reproducible results. The measurement takes place in the cell, using a thin film of oil for wetting surfaces.

8 Claims, 3 Drawing Sheets

U.S. PATENT DOCUMENTS

| | | | | |
|---|---|---|---|---|
| 4,762,798 A * | 8/1988 | Deutsch | 436/67 |
| 4,777,020 A * | 10/1988 | Brigati | 422/99 |
| 4,865,812 A * | 9/1989 | Kuntz et al. | 422/99 |
| 4,950,455 A * | 8/1990 | Smith | 422/56 |
| 4,985,206 A * | 1/1991 | Bowman et al. | 422/99 |
| 5,062,697 A * | 11/1991 | Mitchell | 359/379 |
| 5,074,662 A * | 12/1991 | Sullivan | 356/244 |
| 5,093,268 A * | 3/1992 | Leventis et al. | 436/172 |
| 5,188,963 A * | 2/1993 | Stapleton | 435/288.3 |
| 5,192,503 A * | 3/1993 | McGrath et al. | 422/57 |
| 5,260,032 A * | 11/1993 | Muller | 422/102 |
| 5,290,705 A * | 3/1994 | Davis | 436/164 |
| 5,306,467 A * | 4/1994 | Douglas-Hamilton et al. | 422/99 |
| 5,399,317 A * | 3/1995 | Stolowitz | 422/99 |
| 5,463,223 A * | 10/1995 | Wong et al. | 250/339.12 |
| 5,572,370 A * | 11/1996 | Cho | 359/801 |
| 5,674,457 A * | 10/1997 | Williamsson et al. | 422/102 |
| 5,770,920 A * | 6/1998 | Eckersley et al. | 313/506 |
| 5,897,812 A * | 4/1999 | Kitai et al. | 252/301.4 R |
| 5,958,345 A * | 9/1999 | Turner et al. | 422/104 |
| 5,985,669 A * | 11/1999 | Palander | 436/46 |
| 6,130,056 A * | 10/2000 | Correges | 435/29 |
| 6,207,369 B1 * | 3/2001 | Wohlstadter et al. | 435/6 |
| 6,365,111 B1 * | 4/2002 | Bass | 422/102 |
| 6,417,611 B1 * | 7/2002 | Picht et al. | 313/467 |

OTHER PUBLICATIONS

Schmitz, C. et al., SPIE 1999, 3797, 423-431.*

Sun, T. X. et al, MRS Bulletin 2002, 27, 309-315.*

Lehman, "Dielectric Behavior of Electroiuminescent Zinc Sulfides," *Journal of the Electrochemical Society*, vol. 103, No. 1, pp. 24-29, Jan. 1956.

*Electroluminescent Phosphor Test Procedure (Oil-Suspension Cell Technique)*, Sylvania Technical Information Bulletin, CM-9092 (Dec. 1983).

*Electroluminescent Material for Flat Panel Display*, Final Report for CRADA No. ORNL95-0371, Oct. 2000.

* cited by examiner

TEST CELL FOR EVALUATING PHOSPHOR

BACKGROUND OF THE INVENTION

This invention relates to a method and apparatus for testing phosphor and, in particular, is an improvement on the "oil cell" method used for almost fifty years.

The method and apparatus are described in the context of phosphor for thick film electroluminescent (EL) lamp. Any kind of phosphor can be tested with the new apparatus and method.

An EL lamp is essentially a capacitor having a dielectric layer between two conductive electrodes, one of which is transparent. The dielectric layer can include phosphor particles or there can be a separate layer of phosphor particles adjacent the dielectric layer. The phosphor particles radiate light in the presence of a strong electric field, using relatively little current.

EL phosphor particles are typically zinc sulfide-based materials, including one or more compounds such as copper sulfide ($Cu_2S$), zinc selenide (ZnSe), and cadmium sulfide (CdS) in solid solution within the zinc sulfide crystal structure or as second phases or domains within the particle structure. EL phosphors typically contain moderate amounts of other materials such as dopants, e.g., bromine, chlorine, manganese, silver, etc., as color centers, as activators, or to modify defects in the particle lattice to modify properties of the phosphor as desired. The color of the emitted light is determined by the doping levels. Although understood in principle, the luminance of an EL phosphor particle is not understood in detail. The luminance of the phosphor degrades with time and usage, more so if the phosphor is exposed to moisture or high frequency (greater than 1,000 hertz) alternating current.

The "oil cell" method for testing phosphor typically relies on castor oil as a liquid dielectric in which phosphor particles are dispersed. Suitable electrodes are provided and the phosphor is driven to luminance. Up to a point, the oil cell method provides a quick and convenient way to evaluate new phosphor formulations. The mobility of particles in an electric field in a liquid dielectric is well known; see Lehmann, "Dielectric Behavior of Electroluminescent Zinc Sulfides," *Journal of the Electrochemical Society*, Vol. 103, No. 1, pgs. 24–29, January 1956. This mobility is believed to be one of the causes of unstable and non-reproducible measurements of luminance from an oil cell. The oil cell test method has been found to have almost a ±10% variance in measured luminance even under the most controlled conditions with highly experienced operators.

The variability means that life testing is virtually impossible because the luminance changes over time for reasons having nothing to do with the life of the phosphor. ("Life" is generally accepted to mean the time for luminance to decay to half of initial luminance.)

The variability also means that performing a plurality of tests on a sample is essentially pointless. For example, a series of tests on a single sample is essentially the same as a series of tests on a plurality of samples. Any variation in luminance due to a particular parameter is lost in variations from other causes.

Thin, thick film layers of phosphor are known in the art. As used herein, and as understood by those of skill in the art, "thick-film" refers to one type of EL lamp and "thin-film" refers to another type of EL lamp. The terms only broadly relate to actual thickness and actually identify distinct disciplines. In general, thin film EL lamps are made by vacuum deposition of the various layers, usually on a glass substrate or on a preceding layer. Thick-film EL lamps are generally made by depositing layers of inks on a substrate, e.g. by roll coating, spraying, or various printing techniques. A thin, thick-film EL lamp is not a contradiction in terms and such a lamp is considerably thicker than a thin film EL lamp. Other distinctions between the two types of lamps are described in the report *Electroluminescent Material for Flat Panel Display*, Final Report for CRADA No. ORNL95-0371, October 2000.

U.S. Pat. No. 4,513,023 (Wary) discloses phosphor in a UV curable dielectric layer having a thickness of 0.2–1.2 mils (5.1–30.5 µm). Although phosphor particles in a solid dielectric have less mobility than in a liquid dielectric, the cured layer has a variable thickness across the area thereof, which makes measurements of luminance inconsistent. The option to date, taking phosphor samples and making complete EL lamps, does not guarantee reproducible results and costs considerable time and money.

Thus, the oil cell method and apparatus have been accepted as a quick indication of proof of concept rather than as an analytical tool.

In view of the foregoing, it is therefore an object of the invention to provide a method and apparatus for reproducibly measuring the optical and electrical characteristics of a phosphor.

Another object of the invention is to improve the oil cell test to provide an analytical tool for evaluating phosphor.

A further object of the invention is to provide an oil cell in which the same sample can be tested a plurality of times.

Another object of the invention is to provide an oil cell that can be operated continuously for long periods in order to provide an indication of the operating life of a phosphor.

SUMMARY OF THE INVENTION

The foregoing objects are achieved in this invention in which an test cell is adapted for both making and testing samples. The cell includes a bottom plate and a top plate having concentric apertures defining a central test cavity. A post attached to the bottom plate closes off the bottom of the test cavity. A slide closes off the top of the test cavity. The top of the post is spaced slightly from the underside of the slide to define a test cavity of substantially uniform thickness. The test cavity is filled with phosphor suspended in uncured resin, closed, and the resin is cured. Once cured, the sample is stable, although delicate, and can be re-measured several times with reproducible results. The measurement takes place in the cell, using a thin film of oil for wetting surfaces to improve optical coupling and to eliminate air/dielectric interfaces.

BRIEF DESCRIPTION OF THE DRAWINGS

A more complete understanding of the invention can be obtained by considering the following detailed description in conjunction with the accompanying drawings, in which.

DETAILED DESCRIPTION OF THE INVENTION

Figure 1:
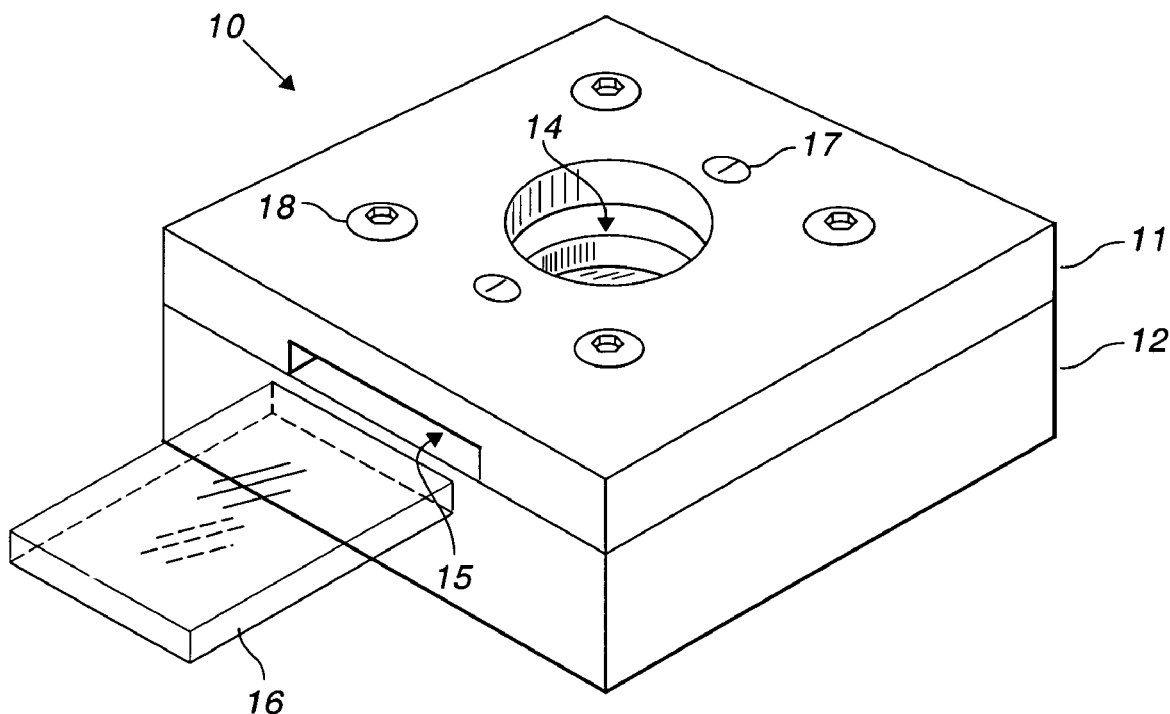
FIG. 1 is a perspective view of an oil cell constructed in accordance with a preferred embodiment of the invention.

FIG. 1 is a perspective view of an oil cell constructed in accordance with a preferred embodiment of the invention. Cell 10 includes top plate 11 made from a suitable plastic such as Plexiglass® acrylate (poly(methyl methacrylate)) or Delrin® acetal resin. Bottom plate 12 is preferably made, from Macor® machinable glass ceramic. Other dimensionally stable, rigid materials could be used instead for either plate. The two plates define central cavity 14 wherein samples are made and tests are performed.

Window 15 is located in one side of top plate 11 and extends to cavity 14. Glass slide 16 fits within window 15 and is inserted into the cell to intersect cavity 14, approximately bisecting the cavity and closing off the upper portion of the cavity. Within cell 10, slide 16 is held in place by set screws, such as set screw 17, which is preferably made from nylon to avoid cracking slide 16. Top plate 11 is fastened to bottom plate 12 by bolts, such as bolt 18.

Figure 2:
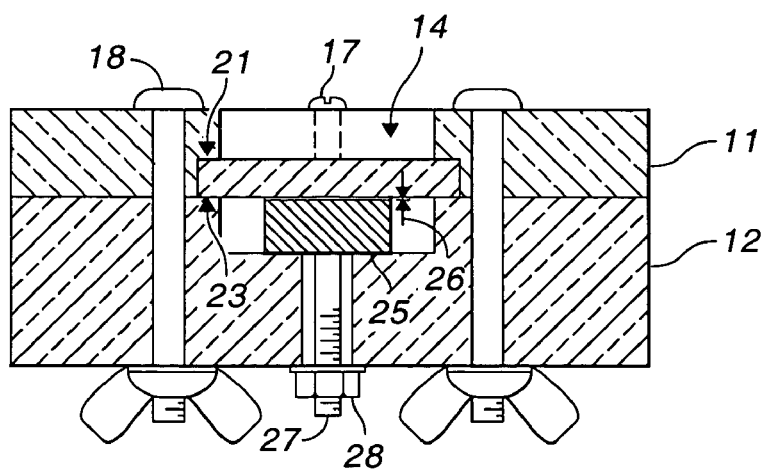
FIG. 2 is a cross-section of an oil cell constructed in accordance with a preferred embodiment of the invention.

FIG. 2 is a cross-section of an oil cell constructed in accordance with a preferred embodiment of the invention and provides a better view of the cavity within cell 10. Top plate 11 is machined or cast in such a way that window 15 (FIG. 1) defines shoulder 21 around cavity 14 for clearing glass slide 16. The portion of cavity 14 in bottom plate 12 is dimensioned to define shoulder 23 for engaging and supporting glass slide 16 when the slide is pushed downward by set screw 17.

The portion of cavity 14 in bottom plate 12 encloses post 25, which is preferably made from stainless steel. The depth of cavity 14 in bottom plate 12 is slightly greater than the height of post 25, leaving gap 26. The area between the upper surface of post 25 and the lower surface of slide 16 has a substantially constant thickness; i.e. the surfaces are substantially parallel.

In one embodiment of the invention, gap 26 was 0.004±0.0001 inches (101.6±2.5 µm). The tolerance figure relates to flatness, not to the size of the gap. A gap in the range of at least 2–8 mils (51–203 µm.) could be used. If gap 26 is larger than a given value, a higher voltage is required for good, measurable, light output. If gap 26 is smaller than a given value, manipulation of the film (described below) becomes more difficult.

Post 25 is held against the bottom of cavity 14 by bolt 27 and washer-nut 28.

The following non-limiting example is presented to illustrate the use of the apparatus. In general, one prepares a thin sample of phosphor in a thick film dielectric resin. Phosphor suspended in uncured resin is placed in the measurement cell and cured in gap 26 to assure uniform thickness of the sample. The test cell acts as a mold for making the sample. The amount of resin and phosphor is chosen to fill the volume above post 26. Once cured, the sample is stable, although delicate, and can be re-measured several times with reproducible results. The measurement takes place in the cell, using a thin film of oil for wetting surfaces to improve optical coupling and to eliminate air/dielectric interfaces. A suitable sensor is placed in the upper portion of cavity 14 for measuring luminosity, color, or other optical characteristics.

Sample Preparation
1. Tare watch glass
2. Weigh out 0.030 g of clear release liner UV resin (e.g. Clear Coat release liner C-2, mfg. by Kolorcure)
3. Weigh out 0.060 g of phosphor powder to make a 2:1 phosphor: UV resin ratio
4. Mix sample thoroughly
5. Place 0.030 g of this mixture onto the cell post
6. Place a clear glass slide onto the cell covering the phosphor mixture
7. Attach the cell cover using 14 in./oz. of torque
8. Place the cell fixture into a UV curing oven using a lamp intensity of 0.4–0.5 Watts/cm$^2$ for 15 seconds
9. Run the sample through the UV oven two times to ensure good curing through the glass slide
10. Disassemble the fixture and carefully remove the glass slide
11. Using a razor blade scraper, carefully scrape the phosphor film off of the glass slide
12. Place the film onto a watch glass and pass through the UV oven two more times at the same conditions as above to post-cure the film
13. Wipe the slide and fixture with acetone to remove any residue before casting the next film
14. Repeat steps 1–12 to cast a second film from the same phosphor mixture
15. Repeat steps 1–13 for all phosphor powder samples to be measured Sample Measurement
1. Place a fraction of a drop of castor oil onto the post
2. Place the phosphor film to be measured onto the post on top of the oil
3. Place a fraction of a drop of castor oil on top of the phosphor film
4. Place a conductive glass slide on top of the phosphor film on the cell
5. Attach the cell cover by first tightening the four wing nuts underneath the cell, then the two set screws on top of the cell measurement cover (use only a light finger tight pressure)
6. Attach the assembled cell to an AC sine wave power source at 380 Vrms/400 Hz
7. Measure the luminance, x-color and y-color of the phosphor sample
8. Detach the measured cell from the power source
9. Disassemble the cell
10. Carefully remove the phosphor film sample from the cell
11. Carefully wipe all oil off of the film, slide and the cell
12. Repeat steps 1–11 for each phosphor film samples to be measured until all samples have been measured three times in a random order
13. Document the three measurements of film 1 and three measurements of film 2 for each phosphor sample mixture
14. Average the median measurements from each of the two films.
15. The average of the two medians is the luminance value that should be reported.

Test Results

Figure 3:
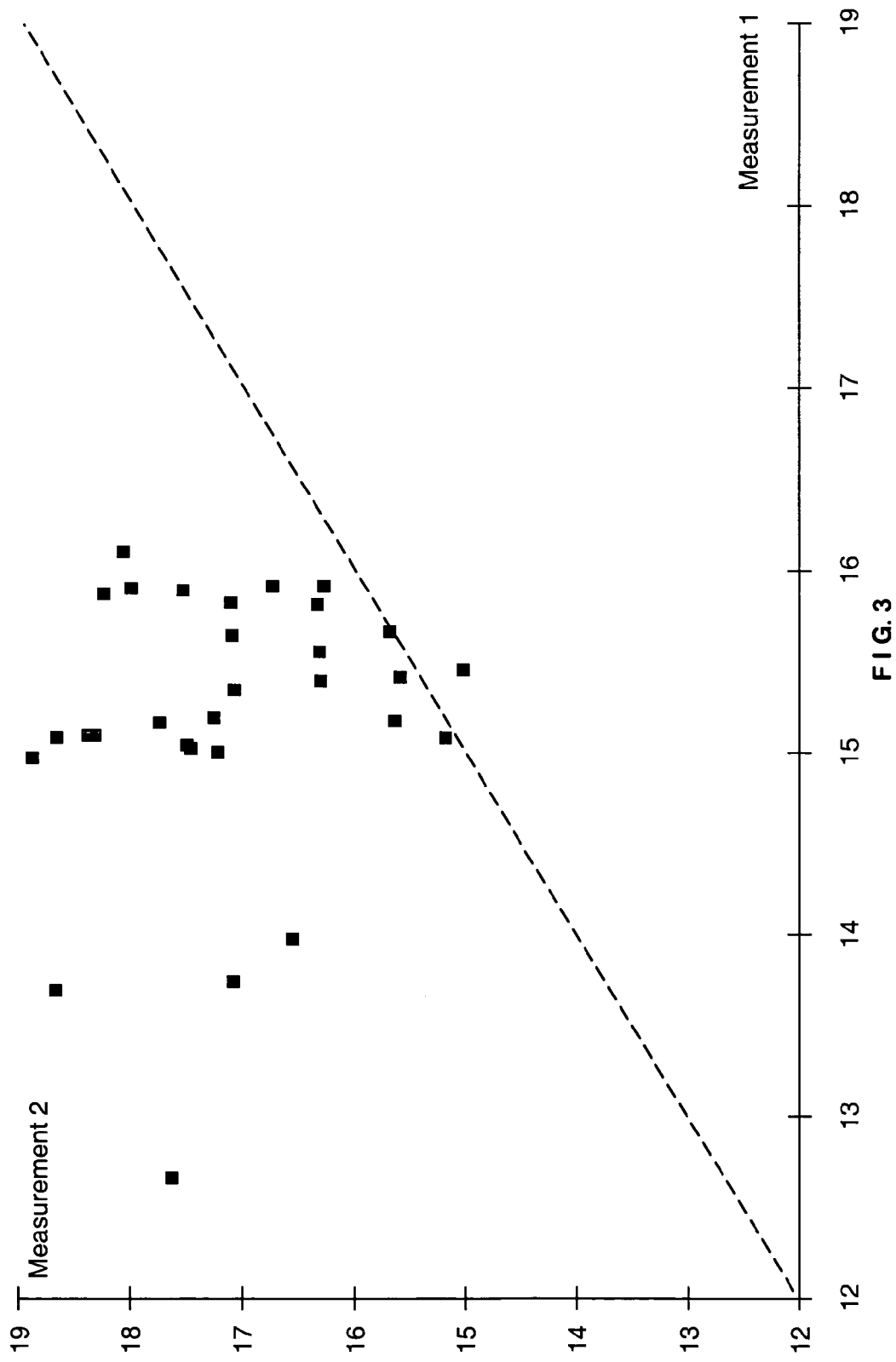
FIG. 3 is a chart illustrating the repeatability of measurements with a test cell constructed in accordance with the prior art.

The following table lists the data from measuring the luminance of thirty samples twice in random order using a test cell constructed in accordance with the prior art. The data is plotted in the chart shown in FIG. 3. Test 1 provides the x coordinate of each data point and test 2 provides the y coordinate of each data point. In a perfect world, x would equal y for each sample and the points would form a straight line along the dashed line shown. As readily seen from FIG. 3, there is a considerable amount of scatter in the data.

| Sample | Test 1 | Test 2 |
|---|---|---|
| 1 | 15.8 | 17.1 |
| 2 | 14.0 | 16.6 |
| 3 | 15.4 | 16.3 |
| 4 | 15.2 | 15.6 |
| 5 | 15.6 | 16.3 |
| 6 | 15.2 | 17.3 |
| 7 | 15.0 | 17.2 |
| 8 | 15.5 | 15.0 |
| 9 | 15.9 | 18.0 |
| 10 | 15.7 | 15.7 |
| 11 | 15.2 | 17.7 |
| 12 | 15.9 | 16.3 |
| 13 | 15.4 | 15.6 |
| 14 | 16.1 | 18.1 |
| 15 | 13.7 | 17.1 |
| 16 | 15.9 | 16.7 |
| 17 | 15.8 | 16.3 |
| 18 | 15.3 | 17.1 |
| 19 | 15.0 | 17.5 |
| 20 | 15.9 | 18.2 |
| 21 | 15.9 | 17.5 |
| 22 | 15.6 | 17.1 |
| 23 | 15.1 | 18.4 |
| 24 | 15.0 | 17.5 |
| 25 | 13.7 | 18.7 |
| 26 | 15.1 | 18.7 |
| 27 | 15.1 | 15.2 |
| 28 | 12.7 | 17.6 |
| 29 | 15.1 | 18.3 |
| 30 | 15.0 | 18.9 |

Figure 4:
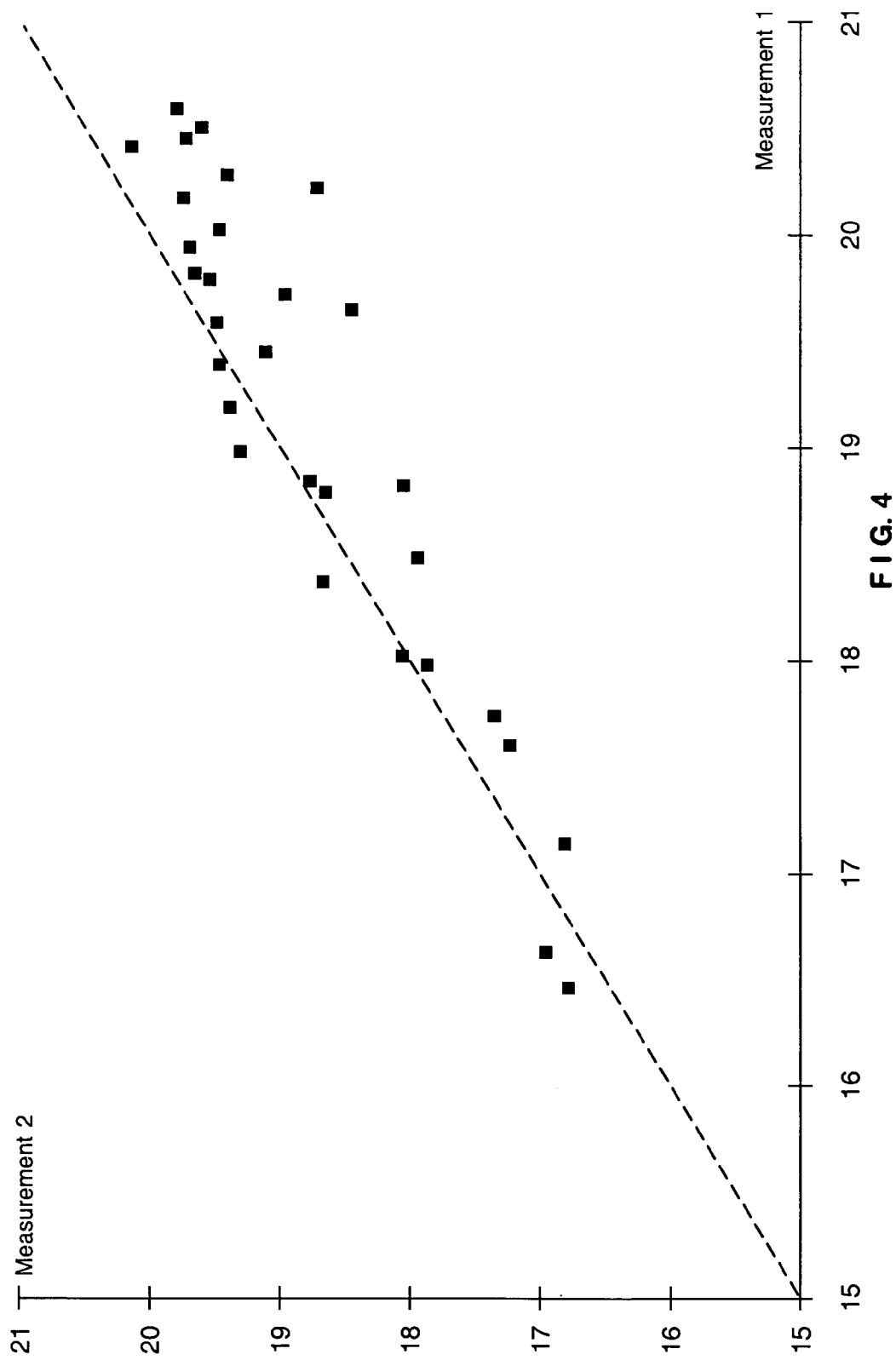
FIG. 4 is a chart illustrating the repeatability of measurements with a test cell constructed in accordance with the invention.

The following table lists the data from measuring the luminance of thirty samples twice in random order using a test cell constructed in accordance with the invention. The data is plotted in the chart shown in FIG. 4. Test 1 provides the x coordinate of each data point and test 2 provides the y coordinate of each data point. Obviously, the data clusters much more closely around the dashed line, indicating a much more accurate measurement.

| Sample | Test 1 | Test 2 |
|---|---|---|
| 1 | 20.22 | 18.72 |
| 2 | 19.45 | 19.11 |
| 3 | 18.02 | 18.06 |
| 4 | 19.79 | 19.54 |
| 5 | 20.59 | 19.79 |
| 6 | 18.98 | 19.30 |
| 7 | 16.63 | 16.96 |
| 8 | 17.74 | 17.35 |
| 9 | 16.46 | 16.78 |
| 10 | 17.60 | 17.23 |
| 11 | 17.98 | 17.87 |
| 12 | 17.14 | 16.81 |
| 13 | 20.45 | 19.72 |
| 14 | 19.94 | 19.69 |
| 15 | 20.02 | 19.46 |
| 16 | 20.41 | 20.14 |
| 17 | 20.17 | 19.74 |
| 18 | 19.65 | 18.45 |
| 19 | 18.37 | 18.67 |
| 20 | 18.82 | 18.05 |
| 21 | 18.79 | 18.65 |
| 22 | 18.48 | 17.94 |
| 23 | 19.82 | 19.65 |
| 24 | 20.50 | 19.60 |
| 25 | 20.28 | 19.40 |
| 26 | 19.19 | 19.38 |
| 27 | 19.59 | 19.48 |
| 28 | 19.39 | 19.46 |
| 29 | 18.84 | 18.77 |
| 30 | 19.72 | 18.96 |

The following table lists the data from measuring the luminance of phosphor that was first tested in November, 2001, using an old test cell of the prior art. That is, the following is old data using the old test cell.

|  | Batch #1 | Batch #3 | Batch #4 |
|---|---|---|---|
|  | 13.50 | 16.77 | 15.53 |
|  | 14.05 | 15.88 | 14.87 |
|  | 14.47 | 16.85 | 15.81 |
|  | 14.26 | 16.96 | 14.61 |
|  | 14.35 | 15.81 | 15.63 |
|  | 13.92 | 15.91 | 15.68 |
|  | 15.02 | 16.65 | 16.62 |
|  | 14.42 | 16.85 | 15.61 |
|  | 14.82 | 15.89 | 16.22 |
|  | 14.27 | 15.75 | 15.57 |
| mean | 14.31 | 16.33 | 15.62 |
| range | 1.52 | 1.21 | 2.01 |
| range as % of mean | 10.6% | 7.4% | 12.9% |

The statistic "range as percent of mean" is used instead of standard deviation because the percent is relative to magnitude whereas standard deviation is affected by frequency of occurrence. The standard deviations for the three columns are 0.43, 0.52, and 0.58, respectively. Note that the column with the smallest standard deviation (Batch #1) does not have the smallest range as a percent of mean (Batch #3). That is, the two statistics are not linearly related, if related at all. The average range as a percent of mean is 10.3 percent.

The same phosphor lot was located and re-measured using a test cell constructed and operated in accordance with the invention. In these tests, the brightness of each film was measured three times. Nine films were made.

| test 1 | test 2 | test 3 | mean | range | range as % of mean |
|---|---|---|---|---|---|
| 10.53 | 10.46 | 10.13 | 10.37 | 0.40 | 3.9% |
| 10.73 | 11.15 | 10.34 | 10.74 | 0.81 | 7.5% |
| 11.79 | 12.25 | 12.57 | 12.20 | 0.78 | 6.4% |
| 11.86 | 11.27 | 11.32 | 11.48 | 0.59 | 5.1% |
| 11.93 | 11.97 | 11.09 | 11.66 | 0.88 | 7.5% |
| 12.94 | 12.10 | 12.17 | 12.40 | 0.84 | 6.8% |
| 10.54 | 11.03 | 11.21 | 10.93 | 0.67 | 6.1% |
| 10.85 | 11.26 | 11.22 | 11.11 | 0.41 | 3.7% |
| 11.81 | 12.96 | 12.23 | 12.33 | 1.15 | 9.3% |
|  |  |  |  | AVG | 6.3% |

The invention thus provides a method and apparatus for reproducibly characterizing a phosphor and enabling one to test a sample a plurality of times. The cell can be operated continuously for long periods in order to provide an indication of the operating life of a phosphor. The cell is much easier to operate and is less prone to error, e.g. by variations in torque on the attaching bolts.

Having thus described the invention, it will be apparent to those of skill in the art that various modifications can be made within the scope of the invention. For example, a fitted disk could be used instead of a slide but this would make the apparatus less easy to use. Other UV resins can be used instead of the disclosed resins. Curing by other mechanisms, e.g. heat or e-beam, can be used instead of UV curing. Other oil can be used instead of castor oil. Other clamping and fastening methods can be used, e.g. a cam type of lock. Other phosphor to resin ratios and voltages can be used within the limit of having sufficient brightness for accurate measurement. It is possible to measure the film that has been cured in the cell without removing it as well; however, re-measurement of the film after removal is not possible without adding at least some oil, which changes luminance.

What is claimed as the invention is:

1. A method for testing phosphor, said method comprising the steps of:
   suspending said phosphor in an uncured dielectric resin;
   curing the resin in a chamber of substantially uniform thickness to produce a sheet of substantially uniform thickness;
   exciting the phosphor to luminance;
   measuring a characteristic of the luminous phosphor in an area of substantially uniform thickness.

2. The method as set forth in claim 1, wherein the phosphor is excited for a sufficient period to determine the life of the phosphor.

3. The method as set forth in claim 1 wherein said characteristic is one of color and brightness.

4. The method as set forth in claim 1 wherein said curing step is followed by the step of post-curing the sheet before exciting the phosphor to luminance.

5. The method as set forth in claim 1 wherein the resin is UV curable and the curing step includes exposing the resin to UV radiation in the chamber.

6. The method as set forth in claim 1 wherein the chamber includes a test cell having a pedestal and a glass slide having flat surfaces defining a space having uniform thickness and wherein said suspending step is followed by the step of placing a quantity of phosphor bearing, uncured resin in the space, thereby filling the space without voids.

7. A test cell for evaluating phosphor, said cell comprising:
   a bottom plate;
   a top plate;
   said bottom plate and said top plate having concentric apertures defining a central test cavity;
   a post attached to said bottom plate for closing off the bottom of the test cavity;
   a slide for closing off the top of the test cavity;
   wherein said post is slightly spaced from said slide to define a gap of substantially uniform thickness for containing a sample of phosphor suspended in cured resin; and
   wherein said top plate includes a window extending from said central aperture to a side thereby providing to the test cavity for said slide.

8. The test cell as set forth in claim 7, wherein said window defines a shoulder for containing said slide.

* * * * *